US00PP28434P2

(12) United States Plant Patent
Brown

(10) Patent No.: US PP28,434 P2
(45) Date of Patent: Sep. 19, 2017

(54) ***SILENE* PLANT NAMED 'SUNSHINE N DAYDREAMS'**

(50) Latin Name: *Silene dioica*
Varietal Denomination: Sunshine n Daydreams

(71) Applicant: Donald R. Brown, Devon (GB)

(72) Inventor: Donald R. Brown, Devon (GB)

( * ) Notice: Subject to any disclaimer, the term of this patent is extended or adjusted under 35 U.S.C. 154(b) by 9 days.

(21) Appl. No.: 14/999,085

(22) Filed: Mar. 29, 2016

(51) Int. Cl.
*A01H 5/02* (2006.01)

(52) U.S. Cl.
USPC ..... Plt./481

(58) Field of Classification Search
USPC ..... Plt./481
See application file for complete search history.

*Primary Examiner* — Susan McCormick Ewoldt
(74) *Attorney, Agent, or Firm* — Bethany R. Roahrig; Barbara Campbell; Cochran Freund & Young, LLC

(57) ABSTRACT

A new cultivar of *Silene* named 'Sunshine n Daydreams' that is characterized by bright golden-yellow foliage and abundant bright pink-red male flowers produced from early summer into fall. 'Sunshine n Daydreams' does not produce seed.

2 Drawing Sheets

Genus and species: *Silene dioica.*
Variety denomination: 'Sunshine n Daydreams'.

BACKGROUND OF THE NEW PLANT

The present invention relates to a new and distinct cultivar of *Silene* plant, known botanically as *Silene dioica* in the family Caryophyllaceae and referred to hereinafter by the cultivar name 'Sunshine n Daydreams'. *Silene dioica*, commonly known as Red Campion, is dioecious (male and female flowers are borne on separate plants). The parents of 'Sunshine n Daydreams' are an unnamed and unpatented golden-foliaged seedling as male parent and an unnamed and unpatented green-foliaged seedling as female parent. 'Sunshine n Daydreams' is an asexually-reproduced selection of a male form of *Silene dioica* and bears only male flowers as disclosed herein.

The inventor has maintained at his nursery in Newton Abbot, Devon, United Kingdom seed lines of *Silene dioica* from the early 1990s. Beginning in 1995, the inventor sought to develop superior forms of the species by interplanting male and female seedlings raised in previous generations. The inventor's objective was to develop robust male forms which would produce pollen and not seeds, and therefore be reproducible only by asexual propagation. Such male forms could also be expected to have larger flowers with successive breeding. In addition, the inventor considered that golden foliage would be a desirable characteristic in combination with the bright pink-red flowers of *Silene.*

In 1995, the inventor identified a weak golden-foliaged male-flowered seedling. The inventor transplanted this weak seedling amongst robust green-foliaged female seedlings. After two generations of seed harvest and resowing, the inventor selected a single seedling, the subject of the present invention.

'Sunshine n Daydreams' was first asexually propagated in 2012 by the inventor at the inventor's nursery in Devon, United Kingdom. Asexual propagation was accomplished using basal shoot cuttings. Since that time, under careful observation, successive generations have been determined fixed, stable and uniform.

SUMMARY

The following traits have been repeatedly observed and represent the distinguishing characteristics of the new *Silene* cultivar 'Sunshine n Daydreams'. These traits in combination set 'Sunshine n Daydreams' apart from all other existing varieties of *Silene* known to the inventor. 'Sunshine n Daydreams' has not been tested under all possible conditions and phenotypic differences may be observed with variations in environmental, climatic and cultural conditions, however, without any variance in genotype.

1. 'Sunshine n Daydreams' exhibits bright golden-yellow foliage.
2. 'Sunshine n Daydreams' produces abundant bright pink-red male flowers in spring and early summer and continues to flower steadily throughout summer and into fall.
3. The plant habit of 'Sunshine n Daydreams' is a compact rosette.
4. A one year old plant of 'Sunshine n Daydreams', grown from a basal shoot cutting is 25 cm to 30 cm in height and in width.
5. A mature plant of 'Sunshine n Daydreams' grown outdoors in good garden soil will remain 30 cm in height foliage mound, excluding flowers, and may spread to 50 cm to 60 cm in diameter.

BRIEF DESCRIPTION OF THE PHOTOGRAPHS

The accompanying color photographs illustrate the overall appearance of the new *Silene* variety 'Sunshine n Daydreams' showing colors as true as it is reasonably possible to obtain in colored reproductions of this type. Colors in the photographs may differ from the color values cited in the detailed botanical description, which accurately describe the actual colors of the new variety 'Sunshine n Daydreams'.

Figure 1:
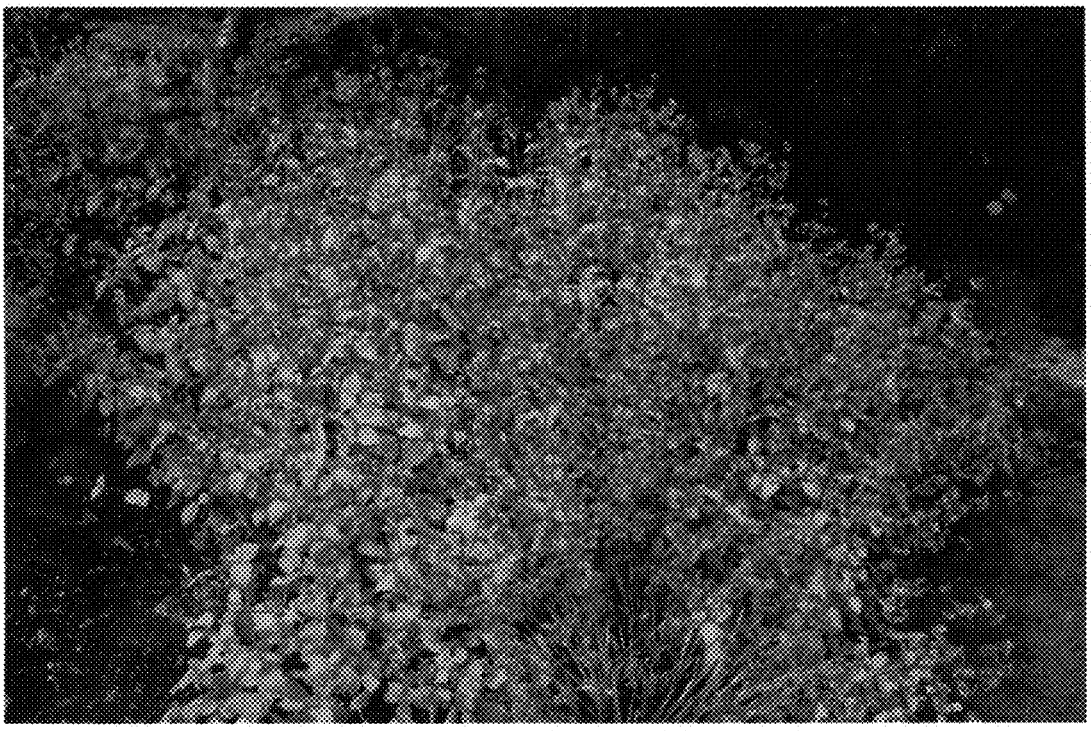
FIG. 1 depicts a two year old plant of 'Sunshine n Daydreams' growing outdoors in the inventor's nursery garden in Newton Abbot, Devon, England. This drawing was made from a photograph taken in August and depicts the low spreading habit of 'Sunshine n Daydreams', the stable golden foliage in summertime and the profuse bright pink-red flowers.
Figure 2:
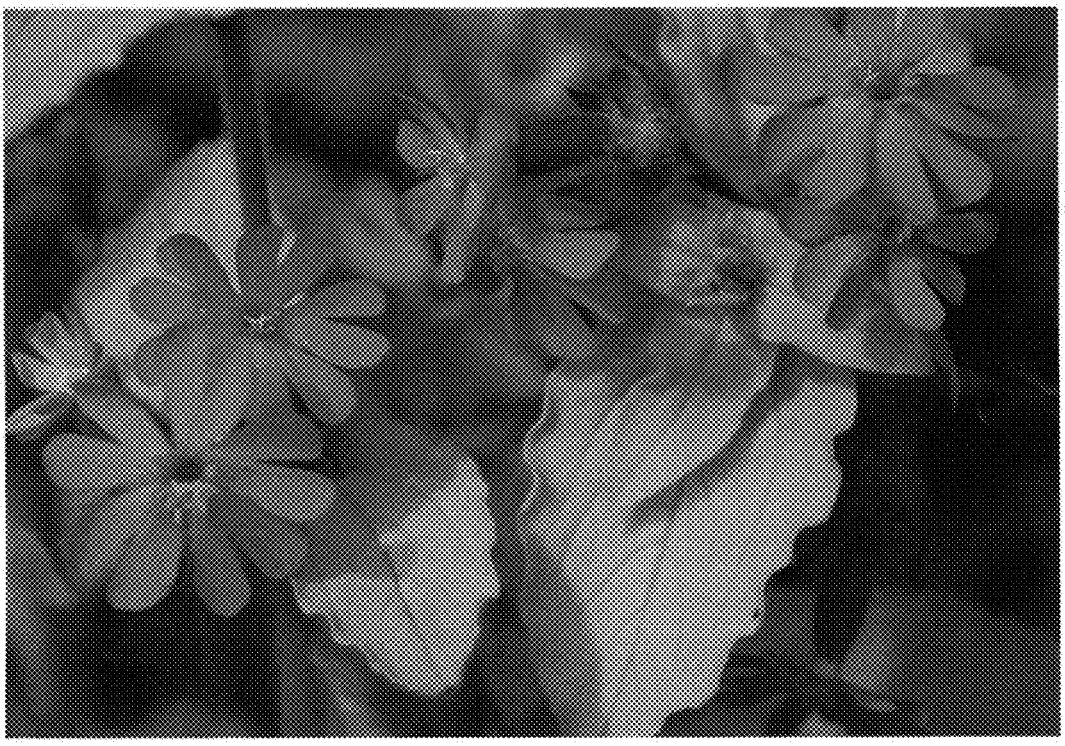
FIG. 2 depicts a close-up view of the golden foliage and the pink-red flowers of 'Sunshine n Daydreams'.

The photographs were made using conventional techniques and although flower and foliage color may appear different from actual color due to light reflectance, they are as accurate as possible by conventional photography.

BOTANICAL DESCRIPTION OF THE PLANT

The following is a detailed botanical description of 'Sunshine n Daydreams'. Data was collected in Santa Barbara, Calif. from one year old plants grown outdoors in a garden border. Color determinations are made in accordance with the 2007 edition of The Royal Horticultural Society Colour Chart, London, England, except where general color terms of ordinary dictionary significance are used. The growing requirements of 'Sunshine n Daydreams' are similar to the species *Silene dioica.*

Botanical classification:

*Family.*—Caryophyllaceae.
*Genus.*—*Silene.*
*Species.*—*dioica.*
*Common name.*—Red Campion.
*Variety.*—'Sunshine n Daydreams'.

Parentage: 'Sunshine n Daydreams' was selected as a seedling from unnamed and unreleased seedlings of male and female forms, having golden and green foliage respectively.

Plant description:

*Use.*—Ornamental.
*Vigor.*—Vigorous.
*Growth habit.*—Compact and clumping.
*Dimensions* (*one year old plants*).—30 cm in height, 30 cm in width.
*Hardiness.*—USDA Zones 4 to 9.
*Propagation.*—Basal cuttings.
*Root system.*—Fibrous.
*Cultural requirements.*—Plant in moisture retentive well-drained soils and full sunlight or partial shade.
*Type.*—Herbaceous perennial.
*Time to initiate roots.*—Approximately 4 to 6 weeks are required for an initial cutting to produce roots.
*Time to develop to a one-gallon container.*—Approximately 6 months are required to produce a finished one-gallon container from a rooted cutting.
*Branching habit.*—Basal rosette.
*Seasonal interest.*—Bright pink-red flowers in spring and summer; golden foliage year round.

Stem:

*Stem shape.*—Cylindrical.
*Color of stem.*—137D.
*Dimensions of stem.*—20 cm to 25 cm in length, 4 mm in diameter.
*Internode distance.*—4 cm to 6 cm.
*Stem surface.*—Villous. Fine silver-gray hairs up to 4 mm in length laying longitudinally against stem surface.

Foliage:

*Type.*—Simple.
*Leaf arrangement.*—Opposite.
*Leaf shape.*—Oblanceolate.
*Leaf base.*—Cuneate.
*Leaf tip.*—Acute.
*Leaf venation.*—Pinnate with depressed veins on adaxial surface and protruding veins on abaxial surface.
*Vein color* (*adaxial and abaxial surface*).—As surrounding leaf surface. Depressed veins on adaxial surface appear darker only by shadow effect. When flattened, veins are barely evident.
*Leaf surface* (*both surfaces*).—Pubescent.
*Leaf attachment.*—Sessile.
*Leaf margin.*—Entire, ciliate with tiny (less than 0.5 mm) silver-gray hairs.
*Leaf dimensions.*—Up to 7 cm. in length and 2 cm. in width.
*Quantity of leaves.*—Approximately 20 leaves per stem.
*Leaf color* (*adaxial surface, full sun*).—Ranges between 1A and 3D.
*Leaf color* (*adaxial surface in partial shade, abaxial surface*).—N144D.

Inflorescence:

*Type.*—Compound cyme.
*Flower type.*—Simple, shape rotate.
*Sexuality.*—Male flowers only are present.
*Flowering period.*—Profusely in spring and early summer, steadily throughout summer and into fall. Flowering is increased in cooler nighttime conditions.
*Lastingness of individual flowers* (*on the plant*).—5 days before fading.
*Persistence.*—Flowers are self-cleaning after fading.
*Flower aspect.*—Facing upward and outward.
*Flower dimensions.*—25 mm in diameter, 18 mm in depth including corolla tube.
*Petals.*—Five, bifid, each pair of lobes fused at and from approximately one third of the base.
*Color of flower petal.*—71C.
*Fused or unfused.*—Petals are unfused.
*Petal surface.*—Glabrous.
*Petal margin.*—Entire.
*Dimensions of petal.*—11 mm in length, 9 mm in width.
*Corona scales.*—Attached where base of petal is fused to corolla tube, appearing as tiny protruding petaloids at mouth of corolla tube.
*Corona scale dimensions* (*where free from tube*).—3 mm in length, 1.5 mm in width.
*Corona scale.*—Shape, oblanceolate; surface, glabrous (both surfaces); color, 71C.
*Depth of corolla tube.*—12 mm.
*Color of corolla tube.*—NN155D.
*Bud color.*—59B.
*Bud dimensions.*—5 mm in length and 4 mm in diameter.
*Shape of bud.*—Oval.
*Surface of bud.*—Silky.
*Persistent or self-cleaning.*—Self-cleaning.
*Calyx.*—Ellipsoidal, 5 fused sepals surrounding corolla tube.
*Calyx dimensions.*—11 mm in length, 5 mm in diameter.
*Calyx color, surface.*—59B, villous, many fine silver-white hairs 1.0 mm to 1.5 mm in length.

*Epicalyx.*—5 unfused bracts.

*Bract dimensions.*—5 mm in length, 3 mm in width.

*Shape of bract.*—Lanceolate.

*Bract color.*—Adaxial surface 187A, abaxial surface N137A.

*Peduncle shape, dimensions.*—Cylindrical, 10 cm to 12 cm in length, 2 mm to 3 mm in diameter.

*Peduncle color, surface.*—Initially N137A becoming 178A. Surface initially villous, becoming smooth as peduncle becomes stiff and wiry.

*Pedicel shape, dimensions.*—Cylindrical, 2.5 cm to 4.0 cm in length, 2 mm to 3 mm in diameter.

*Pedicel color, surface.*—Same as peduncle.

Reproductive organs:

*Stamens.*—Ten in number and unequal in length, 9 mm to 14 mm.

*Form of stamen.*—Longer stamens exserted.

*Color of stamen filament.*—155A.

*Dimensions of stamen.*—6 mm to 9 mm in length and less than 0.5 mm in diameter.

*Anthers.*—Flattened, dorsifixed, color 158A.

*Pollen color.*—158A.

*Amount of pollen.*—Moderate.

Fruit and seed: None observed to date.

Diseases and pests: None known to the inventor.

COMPARISON KNOWN VARIETY

'Sunshine n Daydreams' is markedly more robust than the male parent and differs from the female parent by foliage color. The variety of *Silene* which the inventor considers most closely resembles 'Sunshine n Daydreams' is the inventor's variable seed strain (producing both male and female flowers) known as *Silene* 'Winter Cream'. In addition to its variability as a seed strain, the leaves of 'Winter Cream' become light then mid green as the season progresses, whereas 'Sunshine n Daydreams' continues to produce golden-yellow foliage.

I claim:

1. A new and distinct cultivar of *Silene* plant named 'Sunshine n Daydreams' as described and illustrated herein.

* * * * *